United States Patent [19]

Scherkenbeck et al.

[11] Patent Number: 5,462,955
[45] Date of Patent: Oct. 31, 1995

[54] AZOLYLMETHYL-FLUOROCYCLOPROPYL DERIVATIVES

[75] Inventors: Jürgen Scherkenbeck, Leverkusen; Thomas Himmler, Odenthal; Stefan Böhm, Cologne; Hermann Hagemann, Leverkusen; Klaus Stroech, Solingen; Stefan Dutzmann, Hilden; Heinz-Wilhelm Dehne, Monheim; Gerd Hänssler, Leverkusen, all of Germany

[73] Assignee: Bayer Aktiengesellschaft, Leverkusen, Germany

[21] Appl. No.: 197,016

[22] Filed: Feb. 15, 1994

Related U.S. Application Data

[63] Continuation of Ser. No. 26,663, Mar. 4, 1993, abandoned.

[30] Foreign Application Priority Data

Mar. 13, 1992 [DE] Germany ............... 42 08 050.9

[51] Int. Cl.⁶ ............... A01N 43/653; C07D 249/08
[52] U.S. Cl. ............... 514/383; 514/184; 548/101; 548/267.8; 548/268.6
[58] Field of Search ............... 548/101, 267.8, 548/268.6; 514/184, 383

[56] References Cited

U.S. PATENT DOCUMENTS

| 4,913,727 | 4/1990 | Stroech et al. ............... 71/92 |
|---|---|---|
| 5,146,001 | 9/1992 | Himmler et al. ............... 568/323 |

FOREIGN PATENT DOCUMENTS

| 0047594 | 3/1982 | European Pat. Off. . |
|---|---|---|
| 0080102 | 6/1983 | European Pat. Off. . |
| 0436348 | 12/1990 | European Pat. Off. . |

OTHER PUBLICATIONS

E. J. Corey, *J. Amer. Chem. Soc.*, 1965, pp. 1353–1364.
Teruo Kutsuma, *Heterocycles*, 1977, pp. 397–401.

*Primary Examiner*—Patricia L. Morris
*Attorney, Agent, or Firm*—Sprung Horn Kramer & Woods

[57] ABSTRACT

New azolylmethyl-fluorocyclopropyl derivatives of the formula

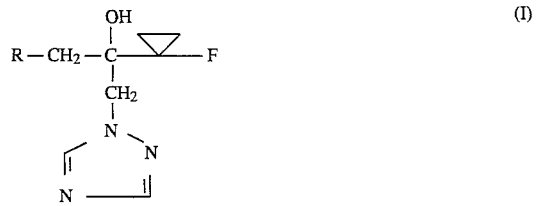

in which
R represents

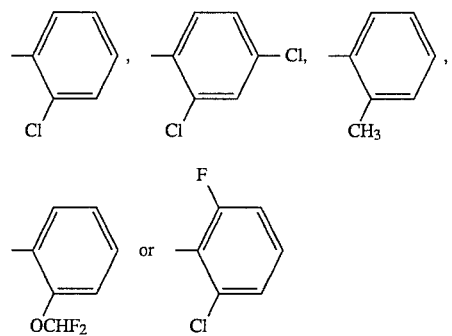

and addition products thereof which acids or metal salts are very effective for combating fungi.

New oxiranes of the formula

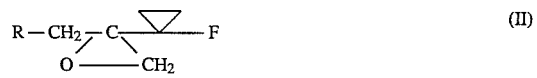

in which
R has the abovementioned meaning, are valuable intermediates for the preparation of compounds of the formula (I).

7 Claims, No Drawings

AZOLYLMETHYL-FLUOROCYCLOPROPYL DERIVATIVES

This application is a continuation of application Ser. No. 08/026,663, filed Mar. 4, 19932, now abandoned.

The present invention relates to new azolylmethyl-fluorocyclopropyl derivatives, to a process for their preparation, and to their use as fungicides.

It has already been disclosed that certain azolylmethyl-cyclopropyl derivatives have fungicidal properties (compare EP-OS (European Published Specification) 0,297,345). For example, 1-(4-chlorophenyl)-2-(1-fluoro-cyclopropyl)-3 -(1,2,4-triazol-1-yl)-propan-2-ol can be used for combating fungi. The action of this substance is good, but sometimes leaves something to be desired when used at low application rates.

New azolylmethyl-fluorocyclopropyl derivatives of the formula

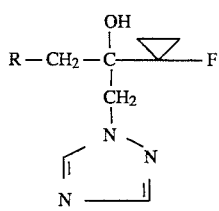

in which p1 R represents

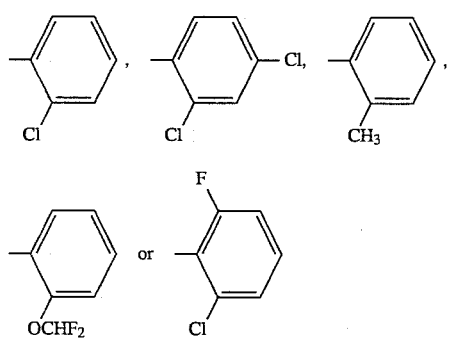

and their acid addition salts and metal salt complexes have now been found.

It has furthermore been found that azolylmethyl-fluorocyclopropyl derivatives of the formula (I) and their acid addition salts and metal salt complexes are obtained when oxiranes of the formula

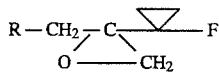 (II)

in which
R has the abovementioned meaning are reacted with 1,2,4-triazole, of the formula

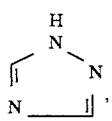 (III)

if appropriate in the presence of an acid-binding agent and in the presence of a diluent, and, if appropriate, an acid or a metal salt are subsequently added onto the resulting compounds of the formula (I).

Finally, it has been found that the new azolylmethylfluorocyclopropyl derivatives of the formula (I) and their acid addition salts and metal salt complexes have very good fungicidal properties.

The substances according to the invention contain an asymmetrically substituted carbon atom. They can therefore be obtained in the forms of optical isomers. The present invention relates to the individual isomers as well as to the mixtures thereof.

Surprisingly, the substances according to the invention have better fungicidal properties than 1-(4-chlorophenyl)-2 -(1-fluoro-cyclopropyl)-3-(1,2,4-triazol-1-yl)propan-2 -ol, which is the active substance of the most similar constitution, has been previously known and has the same direction of action.

Preferred acid addition salts of substances according to the invention are those which are formed by adding the following acids onto azolylmethyl-fluorocyclopropyl derivatives of the formula (I):

Hydrohalic acids such as, for example, hydrochloric acid and hydrobromic acid, in particular hydrochloric acid, furthermore phosphoric acid, nitric acid, sulphuric acid, mono- and bifunctional carboxylic acids and hydroxycarboxylic acids such as, for example, acetic acid, maleic acid, succinic acid, fumaric acid, tartaric acid, citric acid, salicylic acid, sorbic acid and lactic acid, as well as sulphonic acids such as, for example, p-toluenesulphonic acid, 1,5-naphthalene-disulphonic acid and camphorsulphonic acid, saccharin and thiosaccharin.

Preferred metal salt complexes of substances according to the invention are addition products of salts of metals belonging to main group II to IV and sub-group I and II as well as IV to VIII of the Periodic System of the Elements with azolylmethyl-fluorocylopropyl derivatives of the formula (I). Salts of copper, zinc, manganese, magnesium, tin, iron and of nickel are particularly preferred here. Suitable anions of these salts are those which are derived from those acids which lead to physiologically acceptable addition products. Particularly preferred acids of this type are, in this context, the hydrohalle acids such as, for example, hydrochloric acid and hydrobromic acid, furthermore phosphoric acid, nitric acid and sulphuric acid.

If 2-( 2-chlorobenzyl )-2-(1-fluoro-cyclopropyl )-oxirane is used as starting material and 1,2,4-triazole as reactant, the course of the process according to the invention can be illustrated by the following equation:

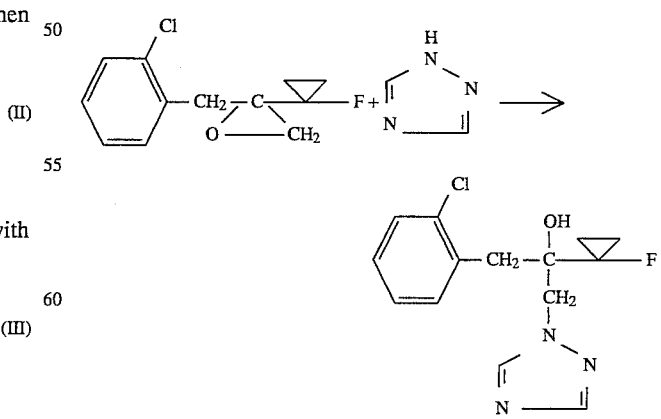

The oxiranes of the formula (II) required as starting materials in the process according to the invention were hitherto unknown. They can be prepared by reacting benzyl ketones of the formula

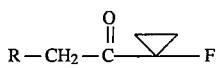 (IV)

in which

R has the abovementioned meaning either α) with dimethyloxosulphoniummethylide, of the formula

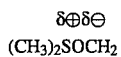 (V)
(CH₃)₂SOCH₂ or β) with dimethylsulphonium methylide, of the formula

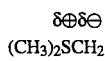 (VI)
(CH₃)₂SCH₂ in the presence of a diluent.

The benzyl ketones of the formula (IV) can be prepared by a) reacting, in a first step benzyl chlorides of the formula R—CH₂Cl (VII)

in which

R has the abovementioned meaning, with an excess of zinc powder in the presence of a diluent such as, for example, ethylene glycol dimethyl ether, at temperatures between 50° C. and 150° C. under a protective gas atmosphere, removing the excess zinc powder, and then b) in a second step, reacting the benzyl derivatives formed, of the formula R—CH₂ZnCl (VIII)

in which

R has the abovementioned meaning, with 1-fluoro-cyclopropane-carboxylic acid chloride of the formula

 (IX)

in the presence of a palladium catalyst such as, for example, bis-(triphenyl-phosphine)-palladium(II) chloride, and in the presence of a diluent such as, for example, ethylene glycol dimethyl ether, at temperatures between 20° C. and 100° C.

The compounds of the formulae (VII) and (IX) are known or can be prepared by processes known in principle (compare EP-OS (European Published Specification) 0,436,348 and EP-OS (European Published Specification) 0,461,483).

Dimethyloxosulphoniummethylide of the formula (V), which is required as reactant for carrying out variant (α) of the process for the preparation of oxiranes of the formula (II), is known (compare J. Am. Chem. Soc. 87, 1363–1364 (1965)). In the above reaction, it is processed in the freshly prepared state, by preparing it in situ by reacting trimethyloxosulphonium iodide with sodium hydride or sodium amide, in particular with potassium tert.-butylate or sodium methylate, or by reacting trimethyloxosulphonium chloride with aqueous sodium hydroxide solution, in each case in the presence of a diluent.

Dimethylsulphonium methylide of the formula (VI), which is furthermore suitable as reactant for carrying out variant (β) of the process for the preparation of oxiranes of the formula (II) is also known (cf. Heterocycles 8, 397 (1977)). In the above reaction, it is also employed in the freshly prepared state, by preparing it in situ, for example from trimethylsulphonium halide or trimethylsulphoniummethylsulphate, in the presence of a strong base such as, for example, sodium hydride, sodium amide, sodium methylate, potassium tert.-butylate or potassium hydroxide, in the presence of a diluent such as tert.-butanol or dimethyl sulphoxide.

Suitable diluents for carrying out the above process for the preparation of oxiranes of the formula (II) are inert organic solvents. The following can preferably be used: alcohols such as tert.-butanol, ethers such as tetrahydrofuran or dioxane, furthermore aliphatic and aromatic hydrocarbons such as benzene, toluene or xylene, and strongly polar solvents such as dimethyl sulphoxide.

When carrying out the above process for the preparation of oxiranes of the formula (II), the reaction temperatures can be varied within a substantial range. In general, the process is carried out at temperatures between 0° C. and 100° C., preferably between 10° C. and 60° C.

When carrying out the above process for the preparation of oxiranes of the formula (II), 1 to 3 moles of dimethyloxosulphonium methylide of the formula (V), or of dimethylsulphonium methylide of the formula (VI), are generally employed per mole of benzyl ketone of the formula (IV). The oxiranes of the formula (II) are isolated by customary methods.

Suitable acid-binding agents for carrying out the process according to the invention are all customary inorganic and organic bases. The following can preferably be used: alkali metal carbonates such as sodium carbonate and potassium carbonate, furthermore alkali metal hydroxides such as sodium hydroxide and potassium hydroxide, furthermore alkali metal alcoholates such as sodium methylate, sodium ethylate, potassium methylate and potassium ethylate as well as potassium tert.-butylate, and furthermore lower tertiary alkylamines, cycloalkylamines and aralkylamines such as, in particular, triethylamine.

Suitable diluents for carrying out the process according to the invention are all customary inert organic solvents. The following can preferably be used: nitriles Such as acetonitrile, furthermore aromatic hydrocarbons, such as benzene, toluene and dichlorobenzene, moreover formamides such as dimethylformamide, as well as strongly polar solvents such as dimethyl sulphoxide and hexamethylphosphoric triamide.

When carrying out the process according to the invention, the reaction temperatures can be varied within a substantial range. In general, the process is carried out at temperatures between 0° C. and 200° C., preferably between 50° C. and 150° C.

When carrying out the process according to the invention, 1 to 4 moles of azole of the formula (III) and 1 to 2 moles of base are preferably employed per mole of oxirane of the formula (II). The end products are isolated in the customary manner.

The azolylmethyl-fluorocyclopropyl derivatives of the formula (I) according to the invention can be converted into acid addition salts or metal salt complexes.

Suitable acids for the preparation of acid addition salts of the compounds of the formula (I) are preferably those which have already been mentioned in connection with the description of the acid addition salts according to the invention as being preferred acids.

The acid addition salts of the compounds of the formula (I) can be obtained in a simple manner by customary salt formation methods, for example by dissolving a compound of the formula (I) in a suitable inert solvent and adding the acid, for example hydrochloric acid, are isolated in a known manner, for example by filtration, and, if appropriate, purified by washing with an inert organic solvent.

Suitable salts of metals for the preparation of metal salt complexes of the compounds of the formula (I) are preferably those which have already been mentioned in connection with the description of the metal salt complexes according to the invention as being preferred metal salts.

The metal salt complexes of the compounds of the formula (I) can be obtained in simple manner by customary processes, for example by dissolving the metal salt in alcohol, for example ethanol, and adding the solution to compounds of the formula (I). Metal salt complexes can be isolated in a known manner, for example by filtration, and, if appropriate, purified by recrystallisation.

The active compounds according to the invention have a powerful microbicidal action and can be employed as fungicides.

Fungicides in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:
Xanthomonas species, such as *Xanthomonas oryzae;*
Pseudomonas species, such as *Pseudomonas lachrymans;*
Erwinia species, such as *Erwinia amylovora;*
Pythium species, such as *Pythium ultimum;*
Phytophthora species, such as *Phytophthora infestans;*
Pseudoperonospora species, such as *Pseudoperonospora humuli* or *Pseudoperonospora cubensis;*
Plasmopara species, such as *Plasmopara viticola;*
Peronospora species, such as *Peronospora pisi* or *P. brassicae;*
Erysiphe species, such as *Erysiphe graminis;*
Sphaerotheca species, such as *Sphaerotheca fuliginea;*
Podosphaera species, such as *Podosphaera leucotricha;*
Venturia species, such as *Venturia inaequalis;*
Pyrenophora species, such as Pyrenophora teres or *P. graminea* (conidia form: Drechslera, syn: Helminthosporium);
Cochliobolus species, such as Cochliobolus sativus (conidia form: Drechslera, syn: Helminthosporium);
Uromyces species, such as *Uromyces appendiculatus;*
Puccinia species, such as *Puccinia recondita;*
Tilletia species, such as *Tilletia caries;*
Ustilago species, such as *Ustilago* nuda or *Ustilago avenae;*
Pellicularia species, such as *Pellicularia sasakii;*
Pyricularia species, such as *Pyricularia oryzae;*
Fusarium species, such as *Fusariumculmorum;*
Botrytis species, such as *Botrytis cinerea;*
Septoria species, such as *Septoria nodorum;*
Leptosphaeria species, such as *Leptosphaeria nodorum;*
Cercospora species, such as *Cercospora canescens;*
Alternaria species, such as *Alternaria brassicae* and
Pseudocercosporella species, such as *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating *Pyricularia oryzae* and *Pellicularia sasakii* on rice, and for combating cereal diseases such as *Leptosphaeria nodorum, Cochliobolus sativus, Pyrenophora teres, Pseudocercosporella herpotrichoides,* Erysiphe and Fusariumspecies. Moreover, they have a very good action against Venturia, Sphaerotheca and Botrytis.

The substances according to the invention can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilisers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomising, scattering, dusting, foaming, brushing on and the like. It is furthermore possible to apply the active compounds by the ultra-low volume method or to inject the active compound formulation or the active compound itself into the soil. The seeds of the plants can also be treated.

On use, the application rate of the substances according to the invention can be raised within a substantial range, depending on the nature of the application method.

For example, in the treatment of parts of plants, the active compound concentrations in the use forms are, in general, between 1 and 0.0001% by weight, preferably between 0.5 and 0.001%. In the treatment of seed, amounts of active compound of 0.001 to 50 g per kilogram of seed, preferably 0.01 to 10 g, are generally required. For the treatment of the soil, active compound concentrations of 0.00001 to 0.1% by weight, preferably 0.0001 to 0.02% by weight, are required at the place of action.

The preparation and the use of the substances according to the invention can be seen from the examples which follow.

Preparation Examples

EXAMPLE 1

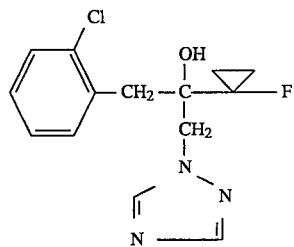
(I-1)

A solution of 5.33 g (23.51 mmol) of 2-(2-chlorobenzyl)-2-(1-fluorocyclopropyl)-oxirane in 15 ml of dimethylformamide is added dropwise at 80° C. with stirring to a mixture of 4.87 g (70.54 mmol) of 1,2,4-triazole and 0.53 g (4.70 mmol) of potassium tert.-butylate in 20 ml of dimethylformamide. When the addition has ended, the reaction mixture is stirred for 6 hours at 80° C. The solvent is subsequently stripped off under reduced pressure, and the residue which remains is taken up in ethyl acetate/water. The aqueous phase is extracted three times using ethyl acetate, and the combined organic extracts are washed once using water. After drying of the organic phase over sodium sulphate and concentration under reduced pressure, the residue is chromatographed on silica gel using the eluent ethyl acetate:cyclohexane=1:2 to 1:1. After evaporation of the eluate, 4.3 g (62% of theory) of 1-(2-chlorophenyl)-2-(1-fluorocyclopropyl)-3 -(1,2,4-triazol-1-yl)-propan-2-ol are obtained in the form of a solid substance of melting point 99 to 103° C.

Preparation of the starting substance:

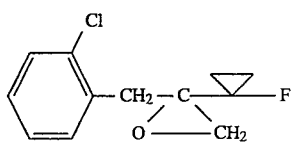
(II-1)

10.3 ml of 45% strength aqueous sodium hydroxide solution are added dropwise at room temperature in the course of one hour to a mixture of 3.33 g (25.86 mmol) of trimethylsulphoxonium chloride and 5.0 g (23.51 mmol) of 2-chlorobenzyl 1-fluorocyclopropyl ketone in 30 ml of toluene. When the addition has ended, stirring is continued for one hour at room temperature. The reaction mixture is diluted with a small amount of water, and the organic phase is separated off. The aqueous phase is extracted three times using cyclohexane. The combined organic extracts are dried over sodium sulphate and concentrated under reduced pressure. The residue is used for the further reaction without additional purification.

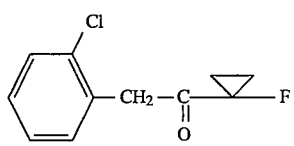
(IV-1)

A mixture of 32.7 g (0.5 mol) of zinc powder, 56.4 g (0.35 mol) of 2-chlorobenzyl chloride and 375 ml of dry ethylene glycol dimethyl ether is refluxed for 2 hours under a nitrogen atmosphere. The reaction mixture is subsequently filtered under nitrogen. The filtrate is treated with 36.7 g (0.3 mol) of 1-fluorocyclopropanecarboxylic acid chloride and 21 mg (0.01 mol %) of bis(triphenylphosphine)-palladium(II) chloride, and refluxed for 2 hours under a nitrogen atmosphere. After cooling to room temperature, the reaction mixture is filtered and then concentrated under reduced pressure. The residue is taken up in toluene, the mixture is extracted by shaking with dilute aqueous hydrochloric acid, the organic phase is dried, and the solvent is stripped off under reduced pressure. The residue which remains is subjected to a fractional distillation. 55.4 g of an oil which, according to gas chromatogram, consists of up to 90% of 2-chlorobenzyl 1-fluorocyclopropyl ketone, are obtained. Accordingly, the yield is calculated as 75% of theory.

reparation of the comparison substance of the formula

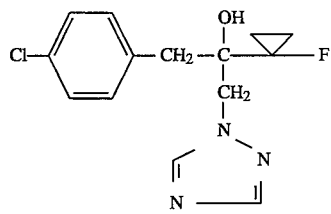

A solution of 3.3 g (15.7 mmol) of 2-(4-chlorobenzyl)-2 -(1-fluorocyclopropyl)-oxirane in 10 ml of dimethylformamide is added dropwise at 80° C. with stirring to a mixture of 3.3 g (47.1 mmol) of 1,2,4-triazole and 0.35 g (3.14 mmol) of potassium tert.-butylate in 20 ml of dimethylformamide. When the addition has ended, the reaction mixture is stirred for 13 hours at 80° C. The solvent is subsequently stripped off under reduced pressure, and the residue which remains is taken up in water. The aqueous phase is extracted four times using dichloromethane. The combined organic phases are dried over sodium sulphate and then concentrated under reduced pressure. The residue which remains is chromatographed on silica gel using the eluent cyclohexane:ethyl acetate=2:1. After evaporation of the eluate, 2.2 g (47% of theory) of 1-(4-chlorophenyl)-2-(1-fluorocyclopropyl)-3-(1,2,4-triazol-1-yl)-propan-2-ol are obtained in the form of a solid.

$^1$H NMR (200 MHz, CDCl$_3$):=δ0.0–0.8 (m, 4H); 3.0 (AB system, 2H); 4.01 (s,1H, OH);

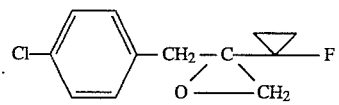

21 ml of 45% strength aqueous sodium hydroxide solution are added dropwise in the course of one hour at room temperature to a mixture of 2.2 g (17.1 mmol) of trimethylsulphoxonium chloride and 3.3 g (15.5 mmol) of 4-chlorobenzyl 1-fluorocyclopropyl ketone in 20 ml of toluene. When the addition has ended, stirring is continued for 2 hours at 40° C. The phases are subsequently separated, and the aqueous phase is extracted three times using toluene. The combined organic phases are washed once with water, dried over sodium sulphate and concentrated under reduced pressure. The residue is used for further reaction without additional purification.

In the use examples which follow, the compound of the formula mentioned below was employed as comparison substance.

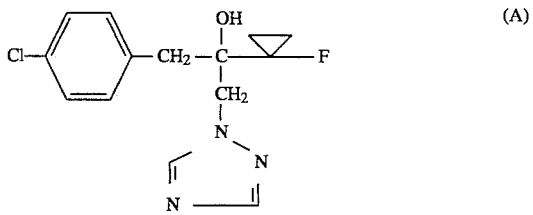

(A)

(Disclosed in EP-OS (European Published Specification) 0,297,345)

Example A

Erysiphe test (barley)/protective

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. *hordei*.

The plants are placed in a greenhouse at a temperature of about 20° C. and a relative atmospheric humidity of about 80%, in order to promote the development of powdery mildew pustules.

Evaluation is carried out 7 days after the inoculation.

In this test, the compound (I-1) according to the invention shows a degree of effectiveness of 100% at a concentration of 250 ppm in the spraying liquid.

Example B

Erysiphe test (wheat)/protective

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. *tritici*.

The plants are placed in a greenhouse at a temperature of about 20° C. and a relative atmospheric humidity of about 80%, in order to promote the development of powdery mildew pustules.

Evaluation is carried out 7 days after the inoculation. In this test, the compound (I-1) according to the invention shows a degree of effectiveness of 100% at a concentration of 250 ppm in the spraying liquid, whereas the comparison substance shows a degree of effectiveness of 85%.

Example C

Erysiphe test (barley)/curative

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are dusted with spores of Erysiphe graminis f.sp. hordei. 48 hours after the inoculation, the plants are sprayed with the preparation of active compound until dew-moist.

The plants are placed in a greenhouse at a temperature of about 20° C. and a relative atmospheric humidity of about 80%, in order to promote the development of powdery mildew pustules.

Evaluation is carried out 7 days after the inoculation. In this test, the compound (I-1) according to the invention shows a degree of effectiveness of 100% at a concentration of 250 ppm in the spraying liquid.

Example D

Erysiphe test (wheat)/curative

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are dusted with spores of *Erysiphe graminis* f.sp. *tritici*. 48 hours after the inoculation, the plants are sprayed with the preparation of active compound until dew-moist.

The plants are placed in a greenhouse at a temperature of about 20° C. and a relative atmospheric humidity of about 80%, in order to promote the development of powdery mildew pustules.

Evaluation is carried out 7 days after the inoculation.

In this test, the compound (I-1) according to the invention shows a degree of effectiveness of 100% at a concentration of 250 ppm in the spraying liquid.

Example E

Fusarium nivale (var. majus) test (wheat)/protective

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Fusarium nivale* (var. *majus*).

The plants are placed in a greenhouse under transparent incubation covers at a temperature of approx. 15° C. under relative atmospheric humidity of approx. 100%.

Evaluation is carried out 4 days after the inoculation.

In this test, the compound (I-1) according to the invention shows a degree of effectiveness of 100% at a concentration of 250 ppm in the spraying liquid, whereas the comparison substance shows a degree of effectiveness of 40%.

Example F

Pyrenophora teres test (barley)/curative

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are sprayed with a conidia suspension of *Pyrenophora teres*. The plants remain in an incubation cabin at 20° C. and 100% relative atmospheric humidity for 48 hours. The plants are then sprayed with the preparation of active compound until dew-moist.

The plants are placed in a greenhouse at a temperature of about 20° C. and a relative atmospheric humidity of about 80%.

Evaluation is carried out 7 days after the inoculation.

In this test, the compound (I-1) according to the invention shows a degree of effectiveness of 100% at a concentration of 250 ppm in the spraying liquid.

Example G

Leptosphaeria nodorum test (wheat)/protective

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a spore suspension of *Leptosphaeria nodorum*. The plants remain in an incubation cabin at 20° C. and 100% relative atmospheric humidity for 48 hours.

The plants are placed in a greenhouse at a temperature of about 15° C. and a relative atmospheric humidity of about 80%.

Evaluation is carried out 10 days after the inoculation.

In this test, the compound (I-1) according to the invention shows a degree of effectiveness of 100% at a concentration of 250 ppm in the spraying liquid.

Example H

Gibberella zeae test (barley)/protective syn. *Fusarium graminearum*

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Gibberella zeae*. The plants are placed in a greenhouse under transparent incubation covers at a temperature of approx. 20° C. under relative atmospheric humidity of approx. 100%.

Evaluation is carried out 4 days after the inoculation.

In this test, the compound (I-1) according to the invention shows a degree of effectiveness of 100% at a concentration of 250 ppm in the spraying liquid.

Example I

Sclerotinia test (dwarf beans)/protective

Solvent: 4.7 parts by weight of acetone

Emulsifier: 0.3 parts by weight of alkyl-aryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small agar pieces covered in growth of *Sclerotinia sclerotiorum* are placed onto each leaf. The inoculated plants are placed in a darkened, humid chamber at 20° C. The size of lesions on the leaves is evaluated 3 days after inoculation.

In this test, the compound (I-1) according to the invention shows a degree of effectiveness of 100% at an active compound concentration of 100 ppm in the spraying liquid.

Example K

Sphaerotheca test (cucumber)/protective

Solvent: 4.7 parts by weight of acetone

Emulsifier: 0.3 parts by weight of alkyl-aryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus Sphaerotheca fuliginea.

The plants are then placed in a greenhouse at 23° to 24° C. and at a relative atmospheric humidity of about 75%.

Evaluation is carried out 10 days after the inoculation.

In this test, the compound (I-1) according to the invention shows a degree of effectiveness of 100% at an active compound concentration of 1 ppm in the spraying liquid.

Example L

Pyricularia test (rice)/protective

Solvent: 12.5 parts by weight: acetone

Emulsifier: 0.3 parts by weight: alkylaryl polyglycol ether

To produce a suitable preparation of active compound, 1 part by weight of active compound is mixed with the stated amounts of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, the compound (I-1) according to the invention, used at a concentration of 0,025% in the spraying liquid, shows a degree of effectiveness of 80%, whereas the comparison substance (A) does not show any activity.

Example M

Pyricularia test (rice)/systemic

Solvent: 12.5 parts by weight: acetone

Emulsifier: 0.3 parts by weight: alkylaryl polyglycol ether

To produce a suitable preparation of active compound, 1 part by weight of active compound is mixed with the stated amounts of solvent, and the concentrate is diluted with water and the stated amount of emulsifier to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, the compound (I-1) according to the invention, at an application rate of 100 mg of active compound per 100 cm², shows a degree of effectiveness of 100%, whereas the comparison substance (A) shows a degree of activity of 50%.

Example N

Pyrenophora tares test (barley)/protective

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to desired concentration.

To test for protective activity, young plants are sprayed with the preparation of active compound until dew-moist. After the spray coating has dried on, the plants are sprayed with a conidia suspension of *Pyrenophora tares*.

The plants then remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, the compound (I-1) according to the invention shows a degree of activity of more than 80% at an active compound concentration of 250 ppm in the spraying liquid, whereas the comparison substance (A) shows a degree of 25%.

Example O

*Fusarium nivale* (var. nivale) test/wheat/protective

To produce a suitable preparation of active compound, sprayable, commercially available active compound formulation is in each case diluted with water to the desired concentration.

To test for protective activity, young plants are sprayed with the preparation of active compound until dewmoist. After the spray coating has dried on, the plants are sprayed with a conidia suspension of Fusarium nivale vat. nivale.

The plants are placed in a greenhouse in translucent incubation chambers at a temperature of about 15° C. and a relative atomspheric humidity of about 100%.

Evaluation is carried out 4 days after the inoculation.

In this test, the compound (I-1) according to the invention shows a degree of activity of 90% at an active compound concentration of 250 ppm in the spraying liquid, whereas the comparison substance (A) shows a degree of activity of 30%.

It is understood that the specification and examples are illustrative but not limitative of the present invention and that other embodiments within the spirit and scope of the invention will suggest themselves to those skilled in the art.

What is claimed is:

1. An azolylmethyl-fluorocyclo-propyl derivative of the formula

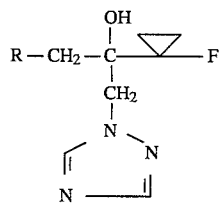

in which

R represents a group of the formula

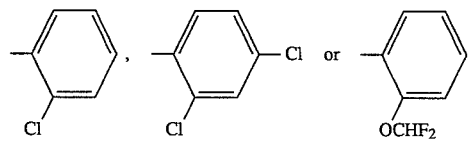

or an addition product thereof with an acid or metal salt.

2. A compound according to claim 1, wherein such compound is 1-(2-chlorophenyl)-2-(1-fluorocyclopropyl)-3-(1,2,4-triazol-1-yl)-propan-2-ol of the formula

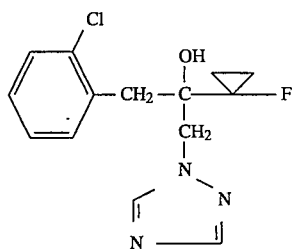

3. A compound according to claim 1, wherein such compound is 1-(2,4-dichlorophenyl)-2-(1-fluorocyclopropyl)-3 -(1,2,4-triazol-1-yl)-propan-2-ol of the formula

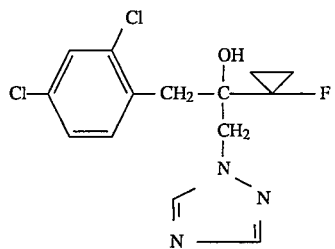

4. A compound according to claim 1, wherein such compound is 1-(2-difluoromethoxy-phenyl)-2 -(1-fluorocyclopropyl)-3-(1,2,4-triazol-1-yl)-propan-2-ol of the formula

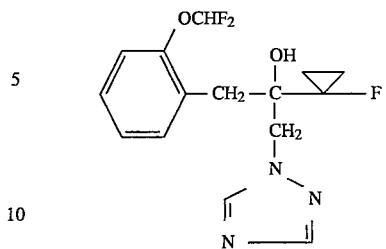

5. A fungicidal composition comprising a fungicidally effective amount of a compound or addition product according to claim 1 and an inert diluent.

6. A method of combating fungi, which method comprises applying to such fungi or to their habitat a fungicidally effective amount of a compound or addition product according to claim 1.

7. A method according to claim 6, wherein such compound is 1-(2-chlorophenyl)-2-(1-fluorocyclopropyl)-3 -(1,2,4-triazol-1-yl)-propan-2-ol, 1-(2,4-dichlorophenyl)-2-(1-fluorocyclopropyl)-3-(1,2,4-triazol-1-yl)-propan-2-ol, 1-(2-difluoromethoxy-phenyl)-2-(1-fluorocyclopropyl)-3 -(1,2,4-triazol-1-yl)-propan-2-ol or.

* * * * *